United States Patent
Oroskar et al.

(10) Patent No.: US 9,291,535 B2
(45) Date of Patent: Mar. 22, 2016

(54) METHOD AND APPARATUS FOR THE EXTRACTION OF VITAMIN D METABOLITES FROM HUMAN PLASMA

(71) Applicant: Orochem Technologies, Inc., Naperville, IL (US)

(72) Inventors: Asha A. Oroskar, Oak Brook, IL (US); Xuejun Zang, Fox Point, WI (US); Javier Ramirez, Round Lake, IL (US)

(73) Assignee: Orochem Technologies, Inc., Naperville, IL (US)

( * ) Notice: Subject to any disclaimer, the term of this patent is extended or adjusted under 35 U.S.C. 154(b) by 25 days.

(21) Appl. No.: 14/340,641

(22) Filed: Jul. 25, 2014

(65) Prior Publication Data

US 2016/0025606 A1    Jan. 28, 2016

(51) Int. Cl.
| | |
|---|---|
| *B01L 9/00* | (2006.01) |
| *G01N 33/92* | (2006.01) |
| *G01N 33/00* | (2006.01) |
| *B01L 3/00* | (2006.01) |
| *G01N 1/40* | (2006.01) |
| *G01N 33/82* | (2006.01) |

(52) U.S. Cl.
CPC .......... *G01N 1/4055* (2013.01); *B01L 3/50255* (2013.01); *G01N 1/4005* (2013.01); *G01N 33/82* (2013.01); *B01L 2200/0631* (2013.01); *B01L 2300/069* (2013.01); *B01L 2300/0681* (2013.01); *B01L 2300/0829* (2013.01); *B01L 2400/049* (2013.01); *B01L 2400/0487* (2013.01); *G01N 2001/4016* (2013.01); *G01N 2001/4061* (2013.01)

(58) Field of Classification Search
CPC ............. G01N 33/92; B01L 9/54; B01L 9/00; B01L 3/502; B01L 3/5085; B01L 3/50; B01L 3/505
USPC ....................... 436/71; 422/430, 50, 68.1, 500
See application file for complete search history.

(56) References Cited

U.S. PATENT DOCUMENTS

| | | |
|---|---|---|
| 2005/0054077 A1 | 3/2005 | Bennett |
| 2006/0105391 A1* | 5/2006 | Engel .................. B01L 3/50255 435/7.1 |
| 2006/0186029 A1* | 8/2006 | Granger ............. G01N 30/6069 210/198.2 |
| 2008/0213906 A1 | 9/2008 | Aurand |
| 2008/0287661 A1 | 11/2008 | Jones |
| 2013/0053588 A1 | 2/2013 | Iraneta |
| 2013/0143329 A1* | 6/2013 | Holmquist ............. G01N 33/82 436/131 |

OTHER PUBLICATIONS

Faria et al, State-of-the-Art in Immobilized Polymer Stationary Phases for High-Performance Liquid Chromatography, J. Braz. Chem. Soc., vol. 20, No. 8, 2009, pp. 1385-1398.*
Al-Qadi et al, Development of High-Performance Liquid Chromatographic Method for Vitamin D3 Analysis in Pharmaceutical Preparation, Jordan Journal of Pharmaceutical Sciences, vol. 3, No. 2, 2010, pp. 78-86.*
Anonymous, "Plate Combines Protein and Phospholipid Removal", CEP Magazine, Mar. 2014, p. 36.
Lone Hymoller and S.K. Jensen,"Vitamin D analysis in plasma by high performance liquid chromatography (HPLC) with C30 reversed phase column and UV detection—Easy and acetonitrile-free", Journal of Chromatography A, 1218 (2011), 1835-1841.

* cited by examiner

*Primary Examiner* — Christine T Mui
(74) *Attorney, Agent, or Firm* — Richard P. Silverman & Assoc., LLC

(57) ABSTRACT

This invention relates to a method and apparatus or kit for extracting major metabolites of vitamin D from human plasma or serum. More particularly, the invention provides for the extraction from human plasma or serum samples comprising vitamin D metabolites such as 1,25-dihydroxy vitamin D3, 25-hydroxy vitamin D2, and D3 from protein binding, removal of protein and phospholipids, and isolation of the metabolites using a combination of ion-exchange and Lewis acid mechanisms without the requirement to acidify the samples. The method and apparatus of the invention comprise a cartridge or plurality of cartridges comprising at least one protein crash frit, a strong cation exchanged sorbent, and an acidified alumina sorbent to provide higher recoveries of vitamin D metabolites than existing phospholipid depletion plate techniques. Accurately quantifying 1,25-dihydroxy vitamin D3 is useful in differential diagnosis of vitamin D-related diseases and for monitoring vitamin D therapy in patients with chronic renal disease.

28 Claims, 4 Drawing Sheets

METHOD AND APPARATUS FOR THE EXTRACTION OF VITAMIN D METABOLITES FROM HUMAN PLASMA

FIELD OF THE INVENTION

The invention relates to a method and an apparatus for extracting the three major metabolites of vitamin D from human plasma or serum. More particularly, the invention provides for the extraction from human plasma or serum samples comprising vitamin D metabolites such as 1,25-dihydroxy vitamin D3, 25-hydroxy vitamin D2, and D3 from protein binding, removal of protein and phospholipids, and isolation of the metabolites using a combination of ion-exchange and Lewis acid mechanisms without the requirement to acidify the samples. The method and apparatus of the invention provides higher recoveries of vitamin D metabolites than existing phospholipid depletion plate techniques. Accurately quantifying 1,25-dihydroxy vitamin D and 25-hydroxy vitamin D metabolites is useful in differential diagnosis of vitamin D-related diseases and for monitoring vitamin D therapy in patients with chronic renal disease.

BACKGROUND

Vitamin D is a steroid hormone which is involved in the human body's system for regulating calcium by influencing the intestinal absorption of calcium and renal re-absorption of calcium. Vitamin D is a fat-soluble hormone that the body can synthesize. There are two major types of vitamin D: vitamin D2 (ergocalciferol), which is synthesized by plants and is not produced by the human body; and vitamin D3 (cholecalciferol), which is made on the human body's skin when exposed to sunlight. Vitamin D binds to two proteins in the bloodstream, albumin and vitamin D binding protein. Once in the bloodstream, the bound vitamin D is transported to the liver, wherein it is transformed into 25-hydroxyvitamin D or calcidiol, which is the primary circulating form of vitamin D and the most commonly measured form in serum. In the kidneys, it is transformed into 1,25 dihydroxy vitamin D or calcitriol, which is the biologically active form of vitamin D.

Vitamin D deficiency is a worldwide problem. It is estimated that over 1 billion people worldwide are either vitamin D deficient or insufficient, including over 40% of elderly US population. Vitamin D is essential for maintaining strong bones because it helps the body use calcium from the diet. Traditionally, vitamin D deficiency has been associated with rickets, a disease in which the bone tissue doesn't properly mineralize, leading to soft bones and skeletal deformities. But increasingly, research indicates the importance of vitamin D in protecting against a number of other health problems. Vitamin D deficiency is associated with hypocalcemia—the presence of low serum calcium levels in the blood, and hypophosphatemia—an abnormally low level of phosphate in the blood, and elevated alkaline phosphatase. Too little vitamin D can pose health risks. Low blood levels of the vitamin have been associated with increased risk of death from cardiovascular disease, cognitive impairment in older adults, severe asthma in children, and cancer. In addition, insufficient intake or production of vitamin D can be caused by a decreased absorption or excessive loss in the gastrointestinal tract, increased vitamin D metabolism, or impaired conversion of vitamin D to 25-hydroxy vitamin D.

Even though 25-hydroxyvitamin D is the preferred vitamin D analyte, measuring it is not straightforward. In serum, the hormone is completely bound to proteins. Furthermore, the normal protein levels in human serum are capable of binding hundreds of nanograms of vitamin D. To measure vitamin D in blood, it must first be released from its binding protein. Analysis methods for vitamin D typically employ LC-MS/MS, liquid chromatography-tandem mass spectrometry analysis protocols. In such protocols the binding protein is precipitated from serum sample. Following the precipitation of the binding protein, the vitamin D is extracted from the sample and then an analysis of organic material is performed. Analytical methods that can accurately and quantitatively identify both forms of vitamin D and their metabolites are essential for diagnosis of vitamin D-related disorders, and for monitoring therapeutic response in patients being treated for vitamin D deficiency.

In pharmaceutical bioanalysis, researchers develop and run various assays to quantitate drugs, pharmaceutical candidates, and their metabolites in biological fluids, such as serum and plasma. The data resulting from these assays are used to help determine the pharmacodynamic and pharmacokinetic properties as well as the toxic and therapeutic concentrations of existing and emerging pharmaceutical compounds in living cells, tissues, and animals. Bioanalytical evaluation is a critical element of the analytical information utilized during the course of drug development, including the pre-clinical stage, the clinical stage, and the therapeutic drug monitoring stage.

Although advances in Liquid Chromatography-Mass Spectrometry (LC-MS) technology have provided improvements in analytical techniques by increasing throughput and improving sensitivity, sample preparation continues to be a critical component of bioanalysis.

The objectives of sample preparation are: 1) concentrating the analyte or analytes of interest; 2) removing interfering compositions which are present in the original sample; and, 3) altering the sample environment to one which is more compatible with the analytical system. Thus the selection of sample preparation techniques range from simple dilution to more elaborate techniques, such as dialysis, ultrafiltration, supercritical fluid extraction, liquid-liquid extraction, and monolithic chromatography. The most widely used techniques in pharmaceutical bioanalysis are protein precipitation, liquid-liquid extraction (LLE), and solid phase extraction (SPE).

Typically, protein precipitation involves dilution of biological samples (e.g. plasma) with a protein precipitating reagent, such as acetonitrile, typically at a volume ratio between 1:3 and 1:4. The diluted sample is vortexed, and the resulting precipitated proteins are removed using filtration or centrifugation methods. The filtrate or supernatant is analyzed without further processing by LC-MS or LC-MS-MS systems. LC-MS-MS, or liquid chromatography-mass spectrometry-mass spectrometry, is an analytical technique in which an additional mass spectrometry is performed on a fragmented ion selected from the first mass spectrometry, and is most often used to sequence peptides. Protein precipitation is relatively simple, and does not require separate procedures for different types of bioanalytical samples. Furthermore, protein precipitation is amenable to high throughput applications which employ automated or computer-directed liquid handlers using multi-well technology. However, there are some major drawbacks to the protein precipitation technique.

Currently, many clinical diagnostic labs still use traditional immunoassays which cannot differentiate between different forms of metabolite, like 25-hydroxy vitamin D2 and 25-hydroxy vitamin D3. LC-MS/MS (liquid chromatography-tandem mass spectrometry) instruments enable a more selective and high sensitive detection method. However, there are problems related to this new technology. Vitamin D metabolites are strongly bonded to proteins in human plasma or serum. Ordinary solid phase extraction or liquid-liquid extract method cannot break this bonding, and therefore cannot completely extract vitamin D metabolites from plasma or serum, directly. Current analytical methods typically require two steps: firstly organic solvents are employed to break the protein bonding, and secondly, the free analytes are further extracted either by solid phase extraction or liquid-liquid extraction techniques. These two step procedures require a lot of sample transferring and labeling. The procedures are time consuming, and these methods cannot be adapted to high volume methods.

Typically, these solid phase extraction (SPE) based methods typically do not completely remove all of the phospholipid compounds, the final results may not be consistent. All vitamin D metabolites and some phospholipid compounds are relatively hydrophobic compounds, and most reversed phase SPE sorbents systems for extraction of the vitamin D metabolites separate the various compounds by hydrophobic interactions. Thus, vitamin D metabolites, especially 25-hydroxy vitamin D, coelute with hydrophobic phospholipids and produce erroneous results. Other methods which employ liquid-liquid extraction to precipitate the protein from the bound vitamin D metabolites are time consuming are subject to handling errors and require frequent maintenance of mass spectrometer equipment to provide consistent results.

US Patent Publication 20080213906 to Supelco discloses a method and device for the preparation of biological samples for subsequent LC-MS analysis using a combined and concurrent protein precipitation and solid phase extraction (SPE) process. The method uses an integrated combination of protein precipitation, filtration, and SPE using a zirconia-coated chromatographic media. According to the method, interfering compounds, such as proteins and phosphate-containing compounds, are eliminated from the biological samples, providing a higher degree of analyte response during LC-MS analysis. The protocol requires adding formic acid to the reagent. According to the method, an organic acid, such as formic acid is required to remove the phosphate compounds.

US Publication No. 2013/0053588 discloses methods, kits and devices for separating phospholipids and proteins from small molecules in biochemical samples. The apparatus includes a wetting barrier, at least one frit and a separation media. The wetting barrier is adapted to 1) retain the liquid sample and a protein precipitating agent in the sample receiving area under a first force, thereby facilitating the formation of a protein precipitate and a processed sample, and 2) flow the processed sample through the wetting barrier and separation media under a second force, wherein the second force is greater than the first force, thereby retaining the protein precipitate in the sample receiving area, retaining phospholipids in the separation media, and eluting small molecules.

Improved methods are sought to free vitamin D metabolites from binding proteins, remove the protein and selectively bind phospholipids so that metabolites of vitamin D can be extracted from serum samples in a single step protocol.

SUMMARY

The process of the present invention relates to an apparatus and a simplified procedure for extracting the three major metabolites of vitamin D from human plasma or serum. The invention provides for the extraction of vitamin D metabolites from human plasma or serum samples comprising vitamin D metabolites such as 1,25-dihydroxy vitamin D3, 25-hydroxy vitamin D2, and D3. The apparatus provides protein binding, removal of protein and phospholipids, and isolation of the metabolites using a combination of protein precipitation, ion-exchange, and Lewis Acid mechanisms without the requirement to acidify the samples. More particularly, the apparatus includes an effective cation exchanged sorbent, such as a strong cation exchanged sorbent or a weak cation exchanged sorbent on an inorganic base such as silica. Most preferably, the effective cation exchanged sorbent is a strong cation exchanged (SCX) silica-based sorbent having a sulfonic group to provide cation exchange stage to ionize the sample and simultaneously bind at least a portion of the phosphatidylcholine groups of the phospholipids, whereby the resulting phospholipids are preferentially retained within the kit, while the vitamin D metabolites pass through the cation exchanged layer to a second sorbent layer containing an acidized sorbent, such as acidized alumina to further isolate and retain phospholipids, while allowing the vitamin D metabolites to be collected. Using the apparatus and process of the present invention small molecules such as caffeine, acetaminophen, hydrocortisone, and carbamazepine can be similarly separated from serum or plasma samples. Thus, the blood or serum sample can be supplied to the apparatus without an acid pretreatment, or an organic acid exchange step. Furthermore, because the sample is non-acidized, or not pretreated with acid, the cost and analysis time of the analysis are reduced, and the potential for contamination is also reduced.

In one embodiment, the invention is an apparatus for isolating metabolites of vitamin D or small molecules from a non-acidized serum or plasma sample comprising proteins, metabolites of vitamin D, small molecules, phospholipids and interfering compounds in an aqueous media. The apparatus comprises:

at least one well having a generally tubular side wall defining an interior well space having an upper inlet and a lower outlet;

a first protein crash frit disposed in the interior well space between the upper inlet and the lower outlet defining an introduction zone above the first protein crash frit and between the upper inlet and the first protein crash frit;

a first sorbent zone comprising a cation exchanged silica sorbent disposed adjacent to and below the first protein crash frit;

a second protein crash frit disposed in the interior well space between the first sorbent zone and the second sorbent zone a second sorbent zone disposed below said first adsorbent zone comprising an acidized alumina sorbent; and, a lower membrane zone being a hydrophobic protein crash plate disposed adjacent to and below the second sorbent zone.

In another embodiment, the present invention a process for isolating metabolites of vitamin D or small molecules from a non-acidized serum or plasma sample comprising proteins, metabolites of vitamin D, small molecules, phospholipids and interfering compounds in an aqueous media. The process comprises a. dispensing an extraction reagent comprising an effective mixture of methanol and acetonitrile to an introduction zone of an apparatus for isolating metabolites of vitamin D or small molecules from a non-acidized serum or plasma sample comprising proteins, metabolites of vitamin D, small molecules, phospholipids and interfering compounds in an aqueous media, wherein said apparatus comprises:

at least one well having a generally tubular side wall defining an interior well space having an upper inlet and a lower outlet;

a first protein crash frit disposed in the interior well space between the upper inlet and the lower outlet defining the introduction zone above the first protein crash frit and between the upper inlet and the first protein crash frit;

a first sorbent zone comprising a cation exchanged silica sorbent disposed adjacent to and below the first protein crash frit;

a second protein crash frit disposed in the interior well space between the first sorbent zone and the second sorbent zone a second sorbent zone disposed below said first adsorbent zone comprising an acidized alumina sorbent; and, a lower membrane zone being a hydrophobic protein crash plate disposed adjacent to and below the second sorbent zone;

b. dispensing a serum or plasma sample to the introduction zone and therein contacting the serum or plasma sample with the extraction reagent to dissociate essentially all of the proteins from the serum or plasma sample;

c. pressurizing the introduction zone to elute a first eluate through the first protein crash frit to provide a first eluate essentially free of proteins;

d. passing the first elute to the first sorbent zone and therein to ionize at least a portion of the first eluate to provide a positively charged eluate and bind portion of the phospholipids.

e. passing the positively charged eluate through a second crash membrane to remove a further portion of the phospholipids and interfering compounds to provide a second eluate;

f. introducing the second eluate to the second sorbent zone further bind phospholipids to provide a second sorbent zone eluate depleted in phospholipids; and g. passing the second sorbent zone eluate through the lower membrane zone to provide a third eluate being essentially free of phospholipids and interfering compounds; and, h. withdrawing the third eluate for further analysis of the metabolites of vitamin D or small molecules.

DETAILED DESCRIPTION OF THE INVENTION

Figure 1:
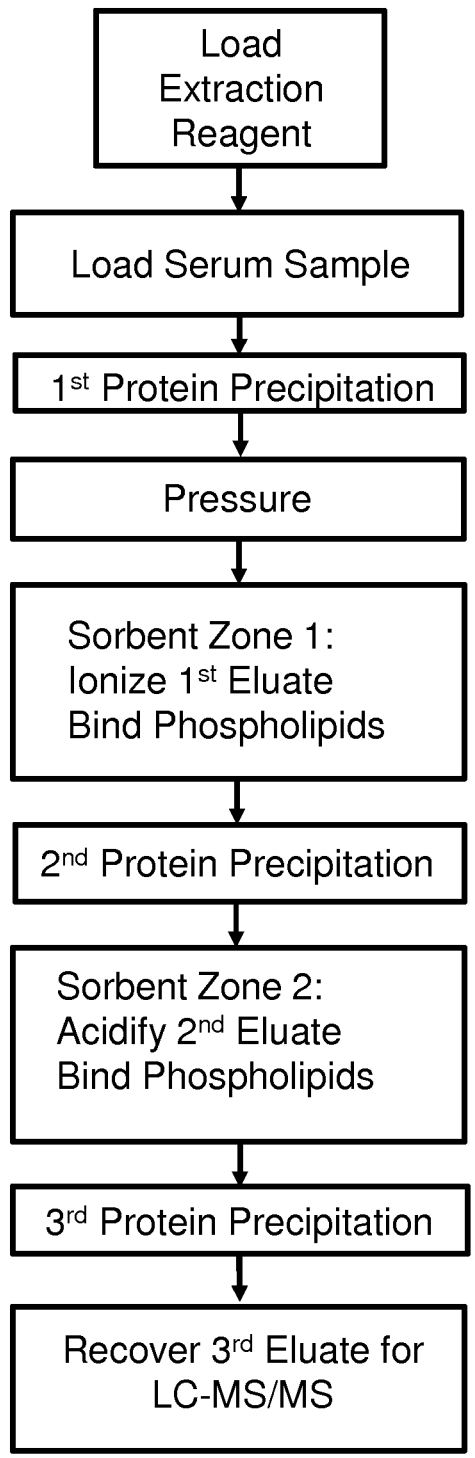
FIG. 1 is a flow chart of the method of the present invention.

In conventional practice, serum or plasma samples are directly acidified to effect protein separation and phospholipid removal prior to any filtration or solid phase extraction. In some methods, the serum or plasma is mixed with an organic acid, such as formic acid, to begin the separation step. An extraction reagent to precipitate the protein may also be added to provide a biological composition. The biological composition, which includes the biological sample mixed with an organic acid and/or protein precipitation agent solution, is introduced into the top of solid phase extraction (SPE) cartridge. The acidified mixture is typically passed through an upper frit, which filters out the precipitated proteins that are suspended in the biological composition. The filtrate of the biological composition next contacts a sorbent comprising a transition metal oxide, which preferentially binds any phosphate-containing compounds, and allows any dissolved analytes to pass through. The biological composition finally contacts the bottom filter, which filters out any remaining precipitated proteins or other particulate matter remaining in the biological composition. The eluate that emerges from the SPE cartridge may then be loaded into a LC-MS or LC-MS-MS device in order to measure any analytes that may be present in the eluate.

The instant apparatus for isolating metabolites of vitamin D or small molecules and associated non-acidized protocol were developed using specific HPLC columns and analytical equipment, using more sensitive analytical equipment should permit the extension of the linearity range beyond the 5-200 ng/mL range with the same inventive apparatus and non-acidized protocol.

In one embodiment, the present invention is a device or kit performing separations of proteins and phospholipids from fluid samples such as serum or plasma comprising solutions or suspensions of those proteins and phospholipids for analyzing for metabolites. A listing of such metabolites includes, but is not limited to, vitamin D metabolites, caffeine, acetaminophen, hydrocortisone, and carbmazephine. Vitamin D metabolites include for example 1,25-dihydroxy vitamin D3, 25-hydroxyvitamin D2 and D3.

The apparatus of the present invention includes a combination of separation media and frits or crash membranes having a specific affinity for phospholipids, and interference compounds. Phospholipids and interference compounds can potentially reduce the accuracy and the sensitivity of the analysis and result in false results. The separation media of the present invention are arranged to provide a synergistic interaction to isolate and separate the phospholipids and other interference compounds from the metabolites of interest. In the present invention, the kit comprises two sorbent zones: a first sorbent zone comprising a first sorbent or a cation exchanged sorbent, and a second sorbent zone comprising a second sorbent to provide a Lewis acid interaction. The cation exchanged sorbent comprises an inorganic base having a positive counter ion which has an organic acid group bonded to the inorganic base. Examples of such cation exchanged sorbents include a silica base exchanged with an acid compound such as sulfonic acid, aromatic sulfonic acid, benzene sulfonate, or polysulfonic acid. Applicants have discovered that a sorbent comprising a silica having a sodium counter ion exchanged with benzene sulfonate provided stability and repeatability. It was found that in the process of the serum or plasma sample passing through the first sorbent zone resulted in at least a portion of the phosphatidylcholine present in the samples as phospholipids being retained on the cation exchanged sorbent. The second sorbent, comprising the Lewis acid interaction comprised a an acidified inorganic compound or an acidified transition metal oxide. It was discovered that an acidized alumina exhibited high affinity for phosphate-containing compounds such as phospholipids which were disposed in the serum and plasma samples. Furthermore, it was discovered that the acidized alumina significantly retained or removed the remaining portion of the phospholipid compounds and other interfering compounds in the sample, while permitting small molecules such as vitamin D metabolites to pass through. The kit of the present invention also includes strategically placed protein crash plates to prevent migration of the sorbent layers and retain any precipitated proteins and any other particulate matter from migrating into the eluate comprising the recovered metabolite.

One further advantage of the present invention is the elimination of the requirement for a pretreatment or acidification step. This permits the serum or plasma sample to be added directly to the extraction cartridge of the present invention. Applicant's kit provides a simplified procedure wherein the use of a particular combination of extraction reagents, the eluate from the kit of the present invention may then be loaded into a LC-MS or LC-MS-MS device in order to measure any analytes that may be present in the eluate. This simplified procedure reduces the cost of analysis, reduces the opportunity for contamination by reducing the number of separate preparation steps, and provides an increased recovery of vitamin D metabolites.

DESCRIPTION OF THE FIGURES

Referring to FIG. 1, a simplified procedure for the preparation of plasma or serum samples for the extraction and analysis of the three major metabolites of vitamin D and/or other small molecules from human plasma or serum. The invention provides for the extraction from human plasma or serum samples comprising vitamin D metabolites such as 1,25-dihydroxy vitamin D3, 25-hydroxy vitamin D2, and D3 from protein binding, removal of protein and phospholipids, and isolation of the metabolites using a combination of ion-exchange and Lewis acid mechanisms without the requirement to acidify the samples in a separate pretreatment step. All steps referred to herein relate to the cartridge as an individual cartridge or individual well 10 of a multi-well plate of the present invention, which is further described in FIG. 2. The cartridge may comprise a circular cross-section or have any other cross-section such as a square or triangular, having an upper section and a lower section. The upper section comprises an introduction zone and the lower section comprises the sorbent zones. The sorbent zones can be separated by frits or protein crash membranes. The lower section terminates in an outlet for removing the eluate from the cartridge. The side walls of the cartridge may be parallel, tapered or expanded to provide a sufficient introduction zone volume. It is preferred that the upper section, or introduction zone, be wider than the lower section (i.e., from the first protein crash frit to the bottom of the cartridge) to provide sufficient flow through the sorbent zones. The side walls should be essentially seamless; that is, if the well is segmented, the segments must be sealed or fused or welded in a manner which will prevent the cartridge from the leaking the serum or plasma sample, either when pressure is applied to the top of the cartridge, or prevent the introduction of external impurities when a vacuum is applied to the bottom of the cartridge. According to one embodiment of the procedure and referring to FIG. 1 and FIG. 2, at least an aliquot of extraction reagent is loaded into an introduction zone 12 of the cartridge 10. Preferably, the extraction reagent is a mixture of methanol and acetonitrile. More preferably, the extraction reagent is a mixture of methanol and acetonitrile having a volume mix ratio of methanol to acetonitrile having a range from 0.8 methanol:1.2 acetonitrile to 1.2 methanol:0.8 acetonitrile. Most preferably, the extraction reagent is a mixture of methanol and acetonitrile having a volume mix ratio of methanol to acetonitrile of 1 methanol:1 acetonitrile. For example, in a 30 mg cartridge, the amount of extraction reagent would be about 0.4 mL. The sample of plasma or serum sample is then loaded or added to the extraction cartridge 10 in the introduction zone 12. The volume E/S ratio of the extraction reagent to sample can range from 6:1 to 3:1, depending upon the nature of the extraction reagent and the sample. For the analysis of vitamin D metabolites, it is preferred that the E/S ratio of extraction reagent to sample volume ranges from about 4.2:1 to 3.8:1, and most preferably, the E/S ratio of extraction reagent to sample volume ranges from about 4:1. Following the loading of the extraction reagent, 0.1 mL of serum or plasma sample is added directly to the extraction reagent in the introduction zone 12. When the serum or plasma sample is loaded to the extraction reagent, any protein released is precipitated on a first protein crash frit 14. Essentially all of the proteins are dissociated from the serum or plasma sample and when positive pressure is applied to the cartridge, a first eluate is withdrawn through the first protein crash frit 14, thus removing at least a portion of precipitated proteins and the first eluate is passed to a first sorbent zone 16. The first sorbent zone 16 contains a cation exchanged adsorbent comprising a strong cation bonded to an inorganic base such as silica having a bonded anion. The bonded anion can be sulfonic acid, aromatic sulfonic acid, benzene sulfonate, or propylsulfonic acid. Preferably, the first sorbent zone contains strong cation exchanged sorbent wherein the strong anion is a benzene sulfonate bonded to silica with Na+ counter ion. In the first sorbent zone, the first eluate is ionized to provide a positively charged eluate and bind a portion of the phospholipids. The positively charged eluate is passed through a second protein crash frit 15 to remove a further portion of the precipitated phospholipids to provide a $2^{nd}$ eluate which is introduced to a second sorbent zone 18. The second sorbent zone 18 contains an acidified sorbent such as acidic alumina to further bind the remaining phospholipids. In the second sorbent zone 18, phospholipids dissociated by the acidic sorbent and other interference compounds are retained in the second sorbent zone 18. The resulting second sorbent zone eluate is passed through a $3^{rd}$ protein crash plate, or lower membrane zone 28 to provide a $3^{rd}$ eluate. The lower membrane zone 28 comprises a hydrophobic, multi-layer composite of at least three membrane layers (20, 22, 24) selected from controlled pore glass, porous polymers, and/or combinations thereof. One example of a hydrophobic protein crash plate or membrane suitable for the present invention is a standard 2 micron hydrophobic graded membrane that is typically used for filtrating precipitated proteins (Orochem protein crash plate, catalog number OC21 PPT20, Available from Orochem Technologies, Inc., IL). The third eluate, being essentially free of phospholipids and interfering compounds is withdrawn from the second sorbent zone 18 through the outlet 26. The third eluate can be recovered and passed directly to LC-MS/MS analysis for determination of vitamin D metabolite levels. Further sample treatment, such as evaporation and reconstitution, may be required or desired prior to analysis of the third eluate. In the analysis of vitamin D metabolites using the kit and procedure of the present invention, at least 90 wt-percent of the phospholipids can be removed from the serum or plasma sample.

Figure 2:
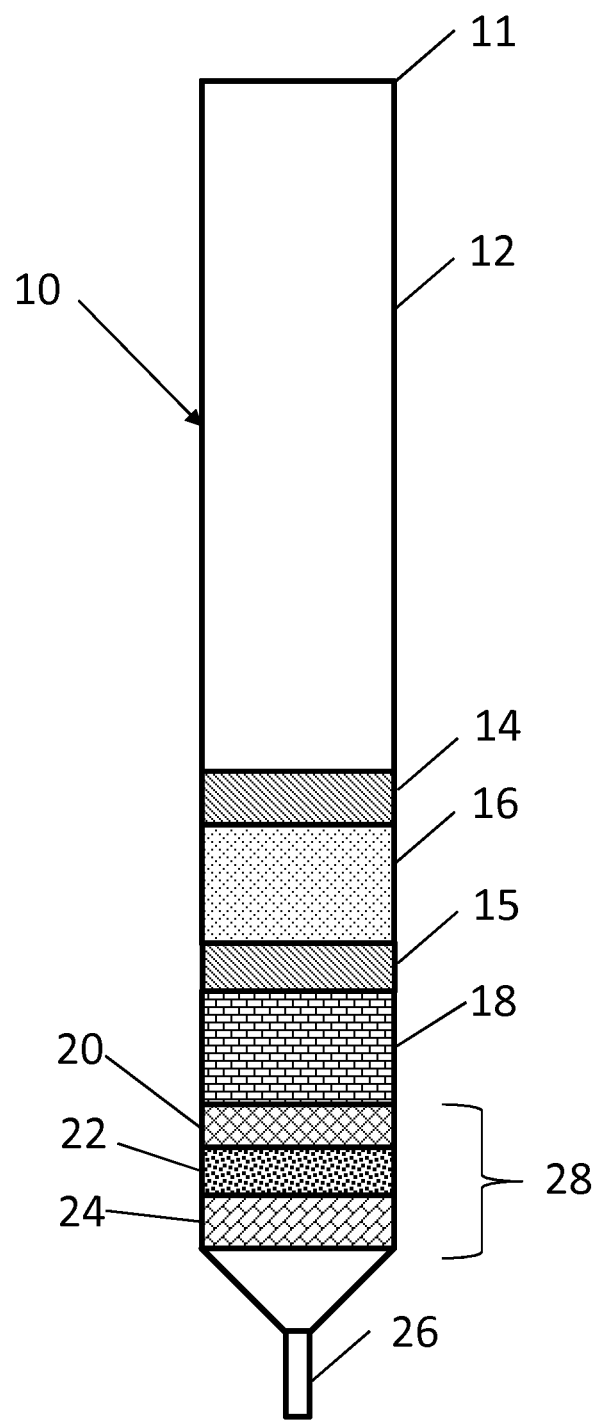
FIG. 2 shows the cartridge, filters and sorbent components of the system of the present invention.

Referring to FIG. 2, shown is a schematic diagram of one embodiment of the invention. In FIG. 2, a cartridge 10, either as a single cartridge, or one of a group of cartridges is shown in cross-section. The cartridge has a generally tubular side wall defining an interior well space having an upper inlet or top 11 and an outlet 26 at the bottom. The cartridge has an introduction zone 10 at the top of the cartridge and the outlet 26 at the bottom of the cartridge 10. Between the introduction zone 10 and the outlet 26 are disposed a series of membranes or frits, and two sorbent zones to facilitate the separation of proteins and the retention of phospholipids from the plasma or serum sample. It is critical for the proper operation of the cartridge that each of the two sorbent zones be preceded by and followed by a membrane or frit plate to prevent leaking and to retain isolated species. The cartridge in practice may be a single well, having a capacity of about 1 mL (or 1 cc) per well and having about 50 mg of sorbent disposed in each of the two sorbent zones, or a multi-well cartridge comprising a plurality of such single wells arrayed in a 96-well plate. Each individual well or individual cartridge 10 comprises a sample introduction zone 12, wherein an extraction reagent and a measured amount of a plasma or serum sample is introduced to the cartridge. Preferably, the volume of the introduction zone 12 comprises between about 60 to about 80 volume percent of the volume of the interior well space. More preferably, the volume of the introduction zone 12 comprises between about two-thirds of the volume of the interior well space. For example, according to the preferred analytical procedure for the invention an aliquot of about 0.4 mL of extraction reagent is loaded into the introduction zone and a 0.1 mL of the plasma or serum sample is loaded into the introduction zone. The first protein crash frit 14 prevents the extraction from leaking beyond the introduction zone during the loading steps. Upon the combination of the extraction reagent and the plasma or serum sample, at least a portion of the proteins in the sample become separated and precipitate on the first protein crash frit 14. Positive pressure is then applied to the cartridge either in the form of direct pressure introduced at the top of the cartridge, by applying vacuum at the outlet 26, or by centrifugation. Again referring to FIG. 2, as positive pressure is applied, a first eluate, being essentially free of proteins is passed through the first protein crash frit 14 to a first sorbent layer 16 consisting of a sorbent comprising a strong cation exchanged adsorbent such as a sulfonic acid bonded on silica in a quantity or residence time sufficient to ionize the first eluate to provide a positively charged eluate. The positively charged eluate is passed through a second protein crash frit 15 to provide a second eluate which is passed to the second layer 18. The second layer 18 contains a second sorbent comprising an alumina acid sorbent to release and retain phospholipids in the second layer 18. A third eluate, withdrawn from the second sorbent zone 18 through a lower membrane zone 28, comprising a multi-layer (20, 22, 24) series of exit membranes selected from porous polymers such as polypropylene, polyethylene (PE), polytetrafluoroethylene (PTFE), glass, and combinations thereof. One example of a hydrophobic protein crash plate suitable for the lower membrane zone 28 of the present invention is a standard 2 micron hydrophobic graded membrane that is typically used for filtrating precipitated proteins (Orochem protein crash plate, catalog number OC21 PPT20, Available from Orochem Technologies, Inc., IL)., is essentially free of phospholipids and other interference compounds. The third eluate can then be passed directly to any bioanalysis procedure including LC-MS/MS.

The first protein crash frit 14 and second protein crash membrane 15 are either depth filters or frits possessing porosities ranging between about 10 µm and about 40 µm. Frits are defined herein as finely porous materials through which liquids may pass. More preferably, the first protein crash frit 14 and second protein crash frit 15 comprise a frit with a porosity ranging between about 10 µm and about 40 µm, and most preferably with a porosity of about 20 µm. The bottom filter 28, more preferably, is a multi-layer filter with a porosity ranging between about 0.2 µm and about 0.45 µm, and most preferably with a porosity of about 0.2 µm.

The first protein crash frit 14 and second protein crash frit 15 are constructed of materials including polypropylene, polyethylene (PE), polytetrafluoroethylene (PTFE), glass, and combinations thereof. PE is a common standard material that provides good aqueous wetting capability and chemical resistance. PTFE offers good chemical resistance and limited "sample leakage" when conducting protein precipitation within a well plate or a cartridge. Most preferably, the first protein crash frit 14 and second protein crash frit 15 are constructed from PE, and the lower filter 28 is constructed as a multi-layer protein crash plate constructed of materials including polypropylene, polyethylene (PE), polyvinylidene difluoride (PVDF), polytetrafluoroethylene (PTFE), glass, and combinations thereof. In one embodiment the multi-layer protein crash plate comprises a first layer 20 at the top comprising PTFE, a second layer 22 comprising PVDF, and a third layer 24 at the bottom comprising a material selected from the group consisting of polypropylene, polyethylene (PE), polyvinylidene difluoride (PVDF), polytetrafluoroethylene (PTFE), glass, and combinations thereof, wherein the multi-layer crash plate has a pore size of from 0.2 to 0.45 µm. An example of such a multi-layer crash plate is a standard 0.2 µm hydrophobic graded membrane that is typically used for filtrating precipitated proteins (Orochem protein crash plate, catalog number OC21 PPT20, Available from Orochem Technologies, IL).

The cartridge 10 is preferably constructed from laboratory grade polypropylene, selected to avoid imparting foreign agents, such as plasticizers, phthalates, long chain hydrocarbons, or mold release agents, into the biological compositions, that could lead to further ion-suppression or ion-enhancement during subsequent LC-MS analysis. Cartridges 10 are selected from a group of containers known in the art, including syringe barrels (without plunger) having volumes ranging between about 0.5 ml and about 60 ml, SPE cartridges with volumes ranging between about 0.5 ml and about 60 ml, and 96-well plates with headspace volume capacities ranging between about 0.5 ml and about 2 ml.

In some embodiments, the invention may comprise two or more cartridges 10 as shown in FIG. 2, and the biological samples may be simultaneously processed in parallel. In one embodiment, each well of a 2, 6, 24, 96, or 192 well plate may be used as cartridges 10.

The precipitated biological sample may be pulled through the extraction cartridges of the present invention via negative pressure using a vacuum manifold common in general SPE and filtration practice. Alternatively, the precipitated biological sample may be pulled through the cartridges of the present invention using a positive pressure SPE manifold commonly used in general SPE and filtration practice. Any method may be used to pull or push the precipitated sample through the cartridges of the present invention, so long as the sample is pulled through the cartridges of the present invention without damaging the cartridge, the sample, or analytes within the sample.

The present invention is further described by the following examples.

EXAMPLES

Example 1

Fortified or spiked human serum having a 100× concentration of a mixture of 1,25-dihydroxy vitamin D3, 25-hydroxy vitamin D2 and D3. The fortified human serum was prepared by diluting the metabolite 1:100 with the serum or plasma. For example, 10 µL of the metabolite mixture was combined with 990 µL of serum to make 1 µg/mL spiked human serum sample. The human serum was obtained from Bioreclamation, LLC, Westbury, N.Y. Extraction reagent in the amount of 0.4 mL was added to the extraction well or cartridge of the present invention. 0.1 mL of the fortified serum sample was added to each well. The extraction reagent in this Example 1 was a 50/50 mixture by volume of methanol and acetonitrile. The extraction cartridge was prepared according to the arrangement shown in FIG. 2. The first sorbent zone contained 50 mg of a strong cation exchanged silica adsorbent and the second sorbent zone contained 50 mg of an acid alumina sorbent. The lower filter was a standard 0.2 µm hydrophobic graded membrane (Orochem Protein Crash Plate, catalog number OC21 PPT20, Available from Orochem Technologies, IL). The first and second protein crash frits were 20 micron PE frits. Positive pressure was applied to the cartridge such that fluid flowed through the extraction cartridge drop by drop, or at a rate of about 0.5 mL/minute and the eluate was collected. The positive pressure was adjusted as required from about 7 to about 28 kPa (1-4 psi). When flow ceased, the positive pressure was raised to a maximum pressure of about 68 kPa and collecting the eluate was continued until no flow was observed, approximately 2 minutes. The vitamin D eluate was evaporated and reconstituted by dissolving the evaporated eluate with 0.1 mL of a solution of 80% acetonitrile in water. The reconstituted sample was then injected to an LC-MS/MS for analysis (Schimazdu HPLC (Available from Shimadzu Scientific Instruments, MD) connected to an AB SCIEX API3000 mass spectrometer (Available from AB SCIEX, Framingham, Mass.). A 20 µL sample of reconstituted vitamin D eluate sample was injected into 3 µm 50×4.6 mm Reliasil C18 HPLC column (Available from Orochem Technologies, Naperville, Ill.). The HPLC mobile phase was an isocratic mobile phase consisted of 90% methanol with 0.1% formic acid and 15 mM ammonium acetate. The Shimazdu HPLC system employed the above isocratic mobile phase at a flow rate of 0.8 mL/min over a run time of 5 minutes. The HPLC operating conditions are show hereinbelow in Table 1.

TABLE 1

| HPLC Column Operating Conditions | |
|---|---|
| Column Temperature | 20 C. |
| Injection Volume | 25 µL |
| Injection Loop | 20 µL |
| Strong Needle Wash | Methanol |
| Weak Needle Wash | Water |
| Strong Needle Wash Volume | 0.5 mL |
| Weak Needle Wash Volume | 0.5 mL |
| Flow Rate | 0.8 mL/min |

Figure 3:
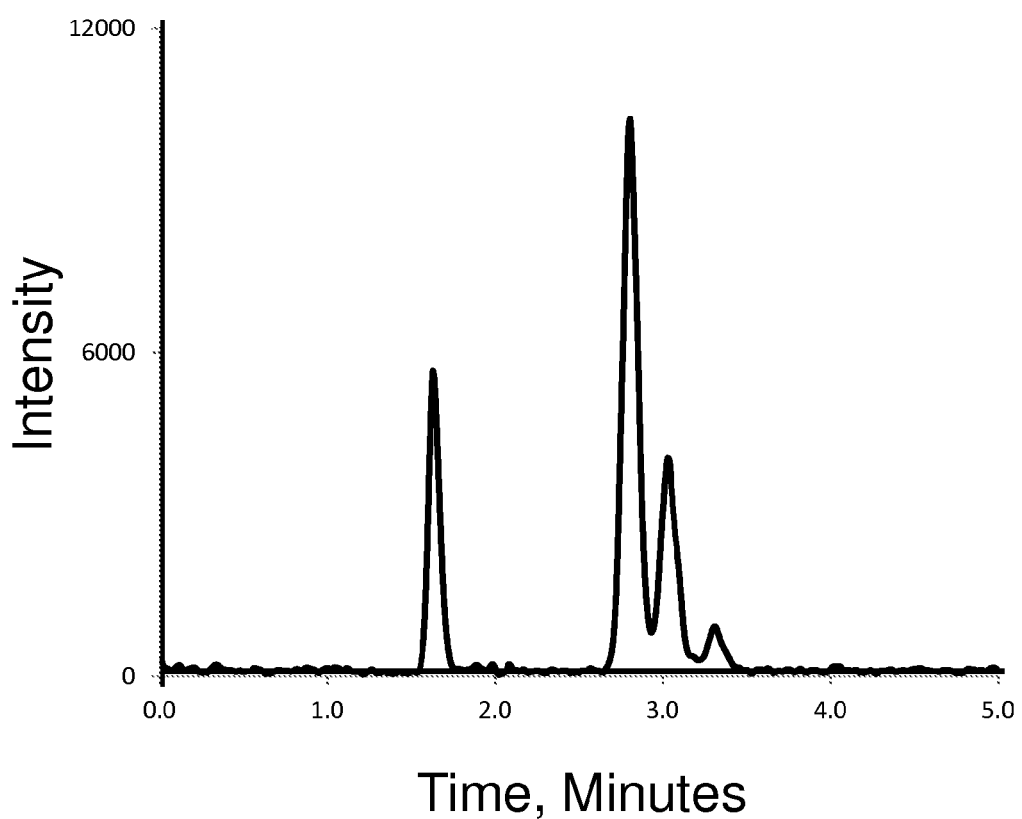
FIG. 3 is a mass chromatogram of vitamin D metabolites extracted from human serum using the present invention.
Figure 4:
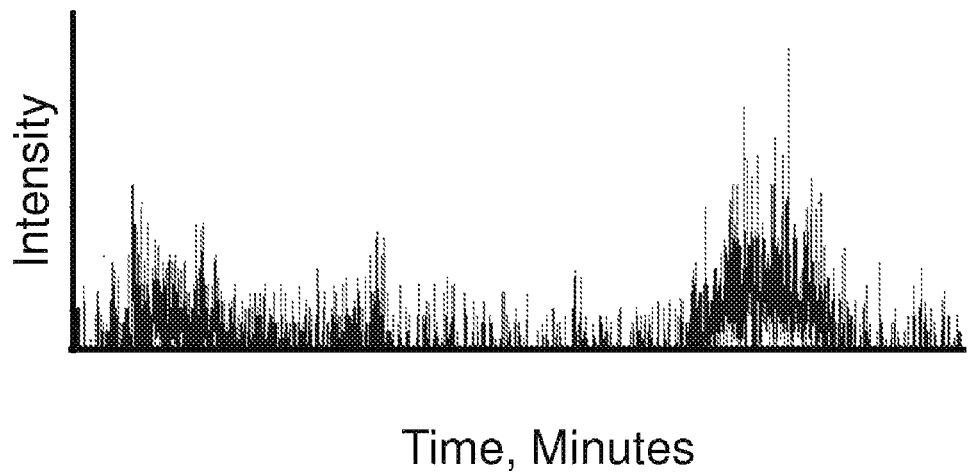
FIG. 4 is a mass chromatogram of the residual phospholipids following extraction using the present invention.

The three metabolites of vitamin D were detected using an AB SCIEX API 3000 mass spectrometer (Available from AB SCIEX, Framingham, Mass.). The multiple reaction monitoring (MRM) transitions of 1,25-dihydroxy vitamin D3, 25-hydroxy vitamin D2, and 25-hydroxy vitamin D3 employed were 434.5-399.3, 430.5-395.2, and 418.5-383.3, respectively. FIG. 3 is a mass chromatogram of the eluate withdrawn from the extraction cartridge of Example 1 for the three metabolites: 1,25-dihydroxy vitamin D3, 25-hydroxy vitamin D2, and 25-hydroxy vitamin D3. The eluate was also analyzed for phospholipid content using the AB SCIEX API 3000 mass spectrometer using a precursor ion scan of 184 m/z, which is believed to be equivalent to the mass-to-charge ratio of phosphatidylcholines, which are believed to account for 60-70% of all of the phospholipids in plasma and serum, and are believed to be responsible for interfering with the analysis for vitamin D metabolites. FIG. 4 shows the mass chromatogram of the phospholipid profile of the phospholipids remaining in the eluate showing the phospholipid peaks of two classes of phospholipids: lypophosphatidylcholine and phosphatidylcholine. Thus, Example 1 demonstrated that using the extraction cartridge, extraction reagent, and procedure of the present invention provided a recovery of 1,25-dihydroxy vitamin D3 of 68 percent by weight with 14% precision, a recovery of 25-hydroxy vitamin D2 of 69 weight percent with 8% precision, and a recovery of 25-hydroxy vitamin D3 of 77 weight percent with 6 percent precision.

Example 2

Selectivity of Strong Cation Exchanged (SCX) Silicas

The procedure of Experiment 1 was repeated varying the type and amount of the strong cation exchange (SCX) sorbent in the first sorbent zone. The strong cation exchange sorbents tested included AGILITY DVB SCX-polymeric ion-exchanged sorbent, CELERITY DVB SCX—a polymeric hydrophilic cation exchanged sorbent, and silica SCX a strong cation exchanged amorphous silica (All available from Orochem Technologies, Inc, Naperville, Ill.). Table 2 shows the results according to the absolute recovery of 1,25-dihydroxy vitamin D3 on a weight basis for varying amounts of the Silica-SCX and the Agility and Celerity sorbents.

TABLE 2

| Recovery as a Function of Amount and Type of Sorbent in First Sorbent Zone | | |
|---|---|---|
| Sorbent Type | Amount of Sorbent, mg | Recovery, wt-% |
| Silica-SCX | 50 | 63 |
| Silica-SCX | 30 | 25 |
| Silica-SCX | 100 | 49 |
| AGILITY-SCX | 50 | 45 |
| CELERITY-SCX | 50 | 29 |

The results show that the strong cation exchange Silica-SCX provided the highest recovery of 1,25-dihydroxy vitamin D3 when the amount of sorbent in the first sorbent layer was equal to the amount of sorbent in the second sorbent zone containing acidified alumina.

Example 3

Phospholipid Sensitivity to Sorbent Zone Variation

Using the procedure of Example 1 and with reference to FIG. 2, the solid extraction exchange cartridge described hereinabove, the phospholipid removal was determined without the silica SCX sorbent, without the acidified alumina and without any sorbents for comparison to the results of Example 1 having both a first and a second sorbent zone. All of the cartridges comprised both a top or first filter, and a lower filter. The top filter was a 20 micron PE frit. The lower filter was a standard 0.2 µm hydrophobic graded membrane (Orochem protein crash plate, catalog number OC21 PPT20, Available from Orochem Technologies, IL). Four cartridges were prepared for this comparison as shown in Table 3.

TABLE 3

| Comparison of Phospholipid Removal Rates Using a Two-Sorbent Zone Cartridge of the Present Invention | | | |
|---|---|---|---|
| Cartridge | Protein Crash Membrane | Silica SCX Sorbent | Acidified Alumina Sorbent |
| A | Yes | 50 mg | None |
| B | Yes | None | 50 mg |
| C | Yes | 50 mg | 50 mg |
| D | Yes | None | None |
| E | Yes | 50 mg* | 50 mg |

*Cartridge E: Inverted Configuration - wherein Alumina sorbent in the upper or $1^{st}$ sorbent zone, SCX sorbent in lower or $2^{nd}$ sorbent zone In all of the cartridges A-E of Example 3, 0.1 mL of the vitamin D fortified serum of Example 1 was mixed with 0.4 mL of the extraction reagent comprising a 50/50 volume ratio mixture of methanol and acetonitrile and the resulting mixture was added to the cartridges A-D. A protein precipitation only control sample, E, was prepared as follows. 0.1 mL of the vitamin D fortified serum of Example 1 was mixed in a microcentrifuge tube with 0.4 mL of the extraction reagent comprising the 50/50 mixture of methanol and acetonitrile centrifuged. The supernate from control sample E was collected and analyzed in the same manner and the eluates from cartridges A-D. The cartridges A-D were processed as in Example 1, and the eluates were collected. The eluates A-E were evaporated and reconstituted by dissolving each of the evaporated eluates with 0.1 mL of a mobile phase comprising 20 vol-% methanol and 80 vol-% acetonitrile. The reconstituted eluates were then injected to an LC-MS/MS for analysis (Schimazdu HPLC connected to an AB SCIEX API 3000 mass spectrometer). The removal rate of the phospholipids is shown in Table 4 hereinbelow:

TABLE 4

Phospholipid Removal

| Cartridge | *Phospholipid Removal, % | Peak Area of Phospholipids |
|---|---|---|
| A | 58 | 1.31e8 |
| B | 27 | 2.29e8 |
| C | 90 | 3.14e7 |
| D | 29 | 2.24e8 |
| E | 69 | 9.8e7 |
| Protein Precipitation Only | — | 3.15e8 |

Note:
Phospholipid removal expressed as a percent is determined by dividing the peak area of the phospholipids in the cartridge by the peak area of the phospholipids by protein precipitation.

Thus, the results of Example 3 showed the cartridge C of the present invention, having the combination of the strong cation exchanged silica in a first sorbent zone and the acidified alumina disposed in a second sorbent zone in a single well provided a significantly larger removal of phospholipids (90 wt-%) than the individual components of the cartridge or the inverted arrangement shown as cartridge E.

Example 4

Extraction Reagent and Recovery of Metabolite

The procedure of Example 1 was repeated with variations in the ratio of the components of extraction reagent. The main components of the extraction reagent of the present invention are methanol and acetonitrile. In this example, extraction reagent mixtures were evaluated for the volume ratio of the extraction reagent to the sample and the effect of the addition of acid to the extraction reagent was observed. As in Example 1, the extraction reagent was first loaded into the cartridges and then 0.1 mL of spiked serum sample was added to each cartridge. Table 5 shows the absolute recovery on a weight basis of 1,25-dihydroxy vitamin D3 for variations in reagent composition, reagent to sample ratio, and acid content.

TABLE 5

Recovery of 1,25-dihydroxy vitamin D3
for Variations in Extraction Reagent Parameters

| Reagent | Reagent to Sample Vol. Ratio | Recovery of Metabolite, % |
|---|---|---|
| Methanol | 3:1 | 30 |
| Methanol | 4:1 | 60 |
| Methanol + 1% Formic acid | 4:1 | 34 |
| Methanol/Acetonitrile (1:1) | 4:1 | 63 |
| Methanol/Acetonitrile (1:1) + 1% Formic Acid | 4:1 | 56 |

The results of Example 4, shown in Table 5, methanol and a 1:1 mixture of methanol and acetonitrile in a reagent and a sample ratio of 4:1 provide significant advantage in the absolute recovery of the vitamin D metabolite. Methanol was found to produce a fine particulate which when used alone resulted in slower flow through the extraction cartridge. Also shown was that the addition of an organic Lewis Acid such as Formic acid actually degrades the performance of the extraction cartridge of the present invention.

Example 5

Comparison of 2-Layer Cartridge with Conventional Single Bed Cartridges for Phospholipid Retention The vitamin D kit performance of the present invention was compared a number of commercially available kits for the analysis of serum and the separation of the resulting eluate from phospholipids. In each test, the manufacturer's protocol was followed. In using the kit of the present invention, no acid was pre-mixed with the serum sample. All of the commercial kits required the pre-mixing of the serum sample with an organic acid such as formic acid. A serum sample of 0.1 mL of the serum spiked with 1,25-dihydroxy vitamin D3 and 25-hydroxy vitamin D2 was loaded into each device. The extraction reagents and the sorbent bed materials used in the devices are summarized in Table 6.

TABLE 6

Test Kit Protocols

| Kit | Sorbent/Layer(s) | | Extraction Reagent |
|---|---|---|---|
| AA | Cation Exchanged Silica | Acidified Alumina | 0.4 mL - 50/50 by vol. Methanol/Acetonitrile |
| BB*** | None | Unknown single layer | 0.4 mL - 1% formic acid in Methanol |
| CC* | None | zirconia bonded onto silica | 0.3 mL - 1% formic acid in Acetonitrile |
| DD** | None | silica bonded with Cl8 | 0.3 mL - 1% formic acid in acetonitrile |

*Note:
as disclosed in U.S. Pat. Publication No. 208213906 to Supelco-HybridSPE Phospholipid plate (50 mg/well, 96-well plate. (Available from Sigma-Aldrich Co, USA)
**Note:
as disclosed in U.S. Pat. Publication No. 201305388 to Waters-Ostro Protein Precipitation and Phosphate Removal Plate(25 mg/well, 96-well-plate(Available from Waters, Milford, Ma, USA)
***Note:
Phenomenex Phree Phospholipid plate (30mg/well, 96-well plate)(Available from Phenomenex, CA, USA)

All of the commercial kits, BB-DD, employed a single sorbent media, and required an organic acid pretreatment step. The procedures were performed as follows:

Kit AA, Present Invention:

For 1 cc cartridges, the extraction reagent (0.4 mL) loaded to the extraction cartridges, and, then the fortified serum sample (0.1 mL) was added to the extraction cartridge(s). After a delay of about 2-3 minutes, positive pressure was to the top of the extraction cartridges, and eluate was collected. As in Example 1, the positive pressure was maintained at about 7-28 kPa (1-4 psi) to provide a drop by drop flow at about 0.5 mL/min while the vitamin D eluate was collected. When flow stopped, the pressure was increased to about 68 kPa (10 psi) to collect the remaining eluate. Collection of the eluate was continued for about 2 minutes after the cessation of flow. The Kit A eluate was evaporated completely at 37° C. by a stream of nitrogen, and the evaporated eluate was reconstituted with 0.1 mL of mobile phase (comprising 20 vol-% methanol and 80 vol-% acetonitrile) and the eluate were injected into the LC-MS/MS for analysis.

Kit BB—30 mg/Well, 96-Well Plate:

The extraction reagent was methanol comprising 1% formic acid. A 0.4 ml quantity of the methanol/formic acid reagent was added to the extraction plate of Kit BB, and then 0.1 mL of the fortified serum sample was added to the plate. After a 2-3 minute wait, positive pressure was applied to the Kit BB plate, and the vitamin D eluate was collected at a rate of about 0.5 mL/min. When flow ceased, the pressure was increased to 69 kPa and the phospholipid eluate was collected. Collection of the eluate was continued until about 2 minutes after the cessation of flow. The Kit BB eluate was evaporated completely at 37° C. by a stream of nitrogen, and the evaporated eluate was reconstituted with 0.1 mL of mobile phase (comprising 20 vol-% methanol and 80 vol-% acetonitrile) and the eluate was injected into the LC-MS/MS for analysis.

Kit CC—50 mg/Well, 96-Well Plate:

The extraction reagent was acetonitrile comprising 1% formic acid. A 0.3 ml quantity of the acetonitrile/formic acid reagent was added to the extraction plate of Kit CC, and then 0.1 mL of the fortified serum sample was added to the plate. After a 2-3 minute wait, positive pressure was applied to the Kit CC plate, and the vitamin D eluate was collected at a rate of about 0.5 mL/min. When flow ceased, the pressure was increased to 69 kPa, and collection of the eluate was continued for about 2 minutes after the cessation of flow. The eluate of Kit CC was evaporated completely at 37° C. by a stream of nitrogen, and the evaporated eluate was reconstituted with 0.1 mL of mobile phase (comprising 20 vol-% methanol and 80 vol-% acetonitrile) and the eluate was injected into the LC-MS/MS for analysis.

Kit DD—25 mg/Well, 96-Well Plate:

The extraction reagent was acetonitrile comprising 1% formic acid. A 0.3 ml quantity of the acetonitrile/formic acid reagent was added to the extraction plate of Kit DD, and then 0.1 mL of the fortified serum sample was added to the plate. After a 2-3 minute wait, positive pressure was applied to the Kit DD plate, and the vitamin D eluate was collected at a rate of about 0.5 mL/min. When flow ceased, the pressure was increased to 69 kPa, and collection of the Kit D eluate was continued for about 2 minutes after the cessation of flow. The Kit DD eluate was evaporated completely at 37° C. by a stream of nitrogen, and the evaporated eluate was reconstituted with 0.1 mL of mobile phase (comprising 20 vol-% methanol and 80 vol-% acetonitrile) and the eluates were injected into the LC-MS/MS for analysis.

A comparison of the performance of the kit of the present invention and the commercial kit is shown in Table 7.

TABLE 7

Comparison of Vitamin D Recovery for Commercial Kits

| Kit | 1,25-dihydroxy vitamin D3 Recovery | 25-hydroxy vitamin D2 Recovery |
| --- | --- | --- |
| AA | 74.0% | 73.0% |
| BB | 36.9% | 14.0% |
| CC | 52.8% | 40.5% |
| DD | 63.5% | 67% |

Thus, in a comparison of a number of commercial vitamin D metabolite kits, Kit AA of the present invention recovered a significantly greater percentage of both 1,25-dihydroxy vitamin D3 and 25-hydroxy vitamin D2 than any other kit tested. Furthermore, the use of the kit of the present invention provided a more simplified and direct protocol for the analysis without the premixing of an organic acid, was required for the other kits tested.

A comparison of the capacity for removal of phospholipids from the serum samples is shown in Table 8. The phospholipid removal percentage was determined as follows:

phospholipid removal rate=(1−phospholipid peak area of test plate/peak area of protein precipitation)/peak area of protein precipitation)*100

The peak area of the protein precipitation was determined by analysis of a supernatant obtained by manually mixing a serum sample with methanol in a 1:4 v/v ratio, centrifuging, and collection the supernatant.

TABLE 8

Comparison of Phospholipid Removal

| Kit | Phospholipid Removal, % |
| --- | --- |
| AA | 90 |
| BB | 94 |
| CC | 99 |
| DD | 98 |

Thus, while the phospholipids were not completely removed by the extraction protocol and extraction cartridge of the present invention in Kit AA, it is believed that a sufficient amount and type phospholipids were removed to provide a higher recovery of the vitamin D metabolites than other kits with higher phospholipid removal rates.

Example 6

Applicability of Kit for Analysis of Other Metabolites

The kit and the procedure of Example 1 was repeated with individually fortified serum samples with small molecule compounds including caffeine, acetaminophen, hydrocortisone, and carbamazepine to verify the viability of using the kit of the present invention and the associated protocol to analyze the presence of these compounds in serum or plasma samples. The procedure employed 1:50 fortified human plasma. The fortified human serum was prepared by diluting the small molecule material 1:50 with the human plasma. The protocol followed the protocol described hereinabove described in Examples 1 and 5 (Kit AA) for the kit of the present invention and without an organic acid pretreatment step. The resulting eluate from each separate small molecule analysis was evaporated by a stream of nitrogen gas at 37° C., and the evaporated material was reconstituted with 0.1 mL of 10% acetonitrile in water. The reconstituted sample was then injected to an LC-MS/MS for analysis (Schimazdu HPLC (Available from Shimadzu Scientific Instruments, MD) connected to an AB SCIEX API3000 mass spectrometer (Available from AB SCIEX, Framingham, Mass.). A 20 mL sample of reconstituted eluate sample was injected into 3 mm 50×4.6 mm Reliasil C8 HPLC column (Available from Orochem Technologies, Naperville, Ill.). The HPLC mobile phase was a gradient from 10% acetonitrile in water for 2 min, then to 70% acetonitrile in 8 minutes. The Shimazdu HPLC system employed the above mobile phase at a flow rate of 0.5 mL/min over a run time of 10 minutes. The HPLC operating conditions were the same as shown in Table 1. The four analytes were detected using an AB SCIEX API 3000 mass spectrometer (Available from AB SCIEX, Framingham, Mass.). The multiple reaction monitoring (MRM) transitions of acetaminophen, caffeine, carbamazepine, and hydrocordisone employed were 151.9→110.0, 195.2→138.1, 237.1→194.0, and 363.1→121.0, respectively. The resulting analysis showed that significant recoveries of these small molecules from the serum sample was possible and precise. Table 9 shows a summary of the results.

TABLE 9

Recovery of Small Molecule Compounds for Using Kit and Protocol of the Present Invention

| Compound | Recovery, % | Precision, % |
|---|---|---|
| Caffeine | 88.0 | 2.3 |
| Acetaminophen | 85.2 | 4.0 |
| Hydrocortisone | 73.2 | 0.9 |
| Carbamazepine | 75.8 | 10.4 |

Example 7

Linearity Study of Method for 5-200 ng/mL Vitamin D Metabolites in Serum

A linearity study was performed to determine the linear reportable range for a vitamin D analyte in human serum using the protocol and apparatus of the present invention. The linearity for each vitamin D analyte was assessed over a broad range for the testing system of the present invention. Accordingly, a set of fortified serum standards containing varying concentrations of vitamin D metabolites ranging from 5 ng/mL to 200 ng/mL (nanograms/milliliter) was prepared to span a broad range of the vitamin D metabolite concentrations. Each vitamin D fortified or spiked human vitamin serum was prepared from a vitamin D free human serum (Available from Golden West Biologicals, Inc. Temecula, Calif.) by adding a 100× concentration of a mixture of 1,25-dihydroxy vitamin D3, 25-Hydroxy(OH) vitamin D3, and 25-Hydroxy(OH) vitamin D2, and diluting it 1:100 with the vitamin D free serum. Accordingly, the 1:100 standard was made by adding a 10 µL portion of the metabolite mixture to 990 µL of the vitamin D free serum to provide a 1 µg/mL spiked vitamin D metabolite standard. The spiked vitamin D metabolite standard was then serially diluted with vitamin D free human serum to provide the following concentrations: 200, 100, 60, 40, 20, 10, and 5 ng/mL, respectively. Each of the serum standards was processed using the procedure of Example 1 to provide 200, 100, 60, 40, 20, 10, and 5 ng/mL evaporated eluate standards. Each of the evaporated eluate standards was mixed with 90 µL of 4-phenyl-1,2,4-triazoline-3,5-dione (PTAD) (1 µg/mL in acetonitrile), vortexed, and incubated at room temperature for one hour. After one hour, 10 µL of water was added to quench the reaction. Each of the mixed evaporated standards was transferred to HPLC vials, injected onto a Waters Acquity UPLC HSS T3 column (Available from Waters Corporation, Milford, Mass.), and analyzed with an Agilent 1290 Infinity UPLC system (Available from Agilent Technologies, Inc., Santa Clara, Calif.). The detailed conditions of the UPLC analysis of the evaporated standards are shown in Table 10, and gradient method employed is shown in Table 11.

TABLE 10

Operating Condition of Agilent UPLC system

| | |
|---|---|
| UPLC Column | Waters Acquity UPLC HSS T3, 1.8 µm, 2.1 × 50 mm |
| Column Temperature | 40° C. |
| Injection Volume | 10 µL |
| Flow Rate | 0.5 mL/min |
| Autosampler Temperature | 4° C. |
| Mobile Phase A | Water with 0.1% formic acid and 0.01 mM methylamine |
| Mobile Phase B | Acetonitrile |

TABLE 11

Gradient Method for Linearity Study

| Time (min) | %B |
|---|---|
| 0.5 | 50 |
| 1.2 | 100 |
| 1.5 | 100 |
| 1.51 | 50 |
| 2.5 | 50 |

With reference to Table 11, the gradient separation is expressed by the volume fraction of the organic solvent in the mobile phase. This volume fraction is shown in Table 11 as % B. Using the above chromatographic conditions shown in Table 10 and gradients shown in Table 11, the metabolite content of each of the evaporated standards was analyzed using an AB Sciex QTrap 6500 Hybrid linear ion-trap triple quadrupole mass spectrometer (Available from AB SCIEX, Framingham, Mass.). The MRM transitions of 25-hydroxy vitamin D2, 25-hydroxy vitamin D3, and 1,25-dihydroxy vitamin D3 derivatives were 619.4→298.1, 607.4→298.1, 635.4→314.1, respectively. Every metabolite's peak area was quantified using Analyst software on the mass spectrometer. The results of the analysis are listed in Table 12. The calibration curve of every metabolite was plot using excel software, x-axis was standard concentration, and y-axis was peak area ratio, and trend line was linear, the R-squared value ($R^2$, coefficient of determination) was calculated by excel software.

TABLE 12

Peak Area Results of over Full Concentration Range
(5-200 ng/mL)

| Standard Concentration (ng/mL) | Peak area of 25-hydroxy vitamin D2 | Peak area of 25-hydroxy vitamin D3 | Peak area of 1,25-dihydroxy vitamin D3 |
|---|---|---|---|
| 200 | 9407000 | 5108400 | 390500 |
| 100 | 3562200 | 2417200 | 214810 |
| 60 | Excluded* | 1755700 | 138210 |
| 40 | 1887600 | 1061500 | 78143 |
| 20 | 365820 | 381210 | 34542 |
| 10 | 72515 | Excluded* | Excluded* |
| 5 |  | 104450 | 15834 |

*excluded outlier of the curve

The results of the peak areas shown in Table 12 demonstrate that the linearity range for 1,25-dihydroxy vitamin D3 is from 5-200 ng/mL, with $R^2=0.994$; for 25-hydroxy vitamin D3 is from 5-200 ng/mL, with $R^2=0.995$; for 25-hydroxy vitamin D2 is from 10-200 ng/mL, with $R^2=0.985$. Although the instant apparatus for isolating metabolites of vitamin D or small molecules and associated non-acidized protocol were developed using specific HPLC columns and analytical equipment, using more sensitive analytical equipment should permit the extension of the linearity range beyond the 5-200 ng/mL range with the same inventive apparatus and non-acidized protocol.

While the disclosure has been described in terms of specific embodiments, it is evident in view of the foregoing description that numerous alternatives, modifications and variations will be apparent to those skilled in the art. Accordingly, the disclosure is intended to encompass all such alternatives, modifications and variations which fall within the scope and spirit of the disclosure and the following claims.

We claim:

1. An apparatus for isolating metabolites of vitamin D or small molecules from a non-acidized serum or plasma sample comprising proteins, metabolites of vitamin D, small molecules, phospholipids and interfering compounds in an aqueous media, said apparatus comprising:
   at least one well having a generally tubular side wall defining an interior well space having an upper inlet and a lower outlet;
   a first protein crash frit disposed in the interior well space between the upper inlet and the lower outlet defining an introduction zone above the first protein crash frit and between the upper inlet and the first protein crash frit;
   a first sorbent zone comprising a cation exchanged silica sorbent disposed adjacent to and below the first protein crash frit;
   a second sorbent zone disposed below said first adsorbent zone comprising an acidized alumina sorbent;
   a second protein crash frit disposed in the interior well space between the first sorbent zone and the second sorbent zone; and,
   a lower membrane zone being a hydrophobic protein crash plate disposed adjacent to and below the second sorbent zone, wherein the hydrophobic protein crash plate is a multi-layer protein crash plate constructed of at least three layers selected from the group consisting of polypropylene, polyethylene (PE), polyvinylidene difluoride (PVDF), polytetrafluoroethylene (PTFE), glass, and combinations thereof.

2. The apparatus of claim 1, wherein the introduction zone has an introduction zone volume comprising between about 60 to about 80 volume percent of the interior well space.

3. The apparatus of claim 1, wherein the first protein crash frit and the second protein crash frit comprise a frit comprising polyethylene or PTFE.

4. The apparatus of claim 1, wherein the first protein crash frit and the second protein crash frit comprise a frit comprising polyethylene and having a porosity of between about 10 µm and about 40 µm.

5. The apparatus of claim 1, wherein first protein crash frit and the second protein crash frit comprise a frit comprising polyethylene and having a porosity of about 20 µm.

6. The apparatus of claim 1, wherein the at least one well is a plurality of wells being disposed on a multi-well plate having 2, 6, 24, 96, or 192 wells.

7. The apparatus of claim 1, wherein the lower membrane zone is a hydrophobic graded membrane.

8. The apparatus of claim 1, wherein the lower membrane zone has a porosity of about 0.2 µm to about 0.45 µm.

9. The apparatus of claim 1, wherein the at least one well is constructed of laboratory grade polypropylene.

10. The apparatus of claim 1, wherein the cation exchanged silica sorbent comprises a strong anion bonded to silica.

11. The apparatus of claim 10, wherein the cation exchanged silica sorbent is benzene sulfonate bonded to silica.

12. The apparatus of claim 1, wherein the generally tubular side wall comprises a cross-section being circular, square, or triangular.

13. The apparatus of claim 1, wherein the generally tubular side wall is parallel, tapered or expanded to provide a sufficient introduction zone volume.

14. The apparatus of claim 1, wherein the generally tubular side is essentially seamless to prevent leaking or the introduction of external impurities on the application of pressure or vacuum.

15. A process for isolating metabolites of vitamin D or small molecules from a non-acidized serum or plasma sample comprising proteins, metabolites of vitamin D, small molecules, phospholipids and interfering compounds in an aqueous media, said process comprising:
   a. dispensing an extraction reagent comprising an effective mixture of methanol and acetonitrile to an introduction zone of an apparatus for isolating metabolites of vitamin D or small molecules from a non-acidized serum or plasma sample comprising proteins, metabolites of vitamin D, small molecules, phospholipids and interfering compounds in an aqueous media, wherein said apparatus comprises:
      at least one well having a generally tubular side wall defining an interior well space having an upper inlet and a lower outlet;
      a first protein crash frit disposed in the interior well space between the upper inlet and the lower outlet defining the introduction zone above the first protein crash frit and between the upper inlet and the first protein crash frit;
      a first sorbent zone comprising a cation exchanged silica sorbent being a benzene sulfonate bonded to silica disposed adjacent to and below the first protein crash frit;
      a second sorbent zone disposed below said first adsorbent zone comprising an acidized alumina sorbent;
      a second protein crash frit disposed in the interior well space between the first sorbent zone and the second sorbent zone; and,
      a lower membrane zone being a hydrophobic protein crash plate disposed adjacent to and below the second sorbent zone wherein the lower membrane zone is a multi-layer protein crash plate constructed of at least three layers selected from the group consisting of polypropylene, polyethylene (PE), polyvinylidene difluoride (PVDF), polytetrafluoroethylene (PTFE), glass, and combinations thereof;

b. dispensing a serum or plasma sample to the introduction zone and therein contacting the serum or plasma sample with the extraction reagent to dissociate essentially all of the proteins from the serum or plasma sample;

c. pressurizing the introduction zone to elute a first eluate through the first protein crash frit to provide a first eluate essentially free of proteins;

d. passing the first elute to the first sorbent zone and therein to ionize at least a portion of the first eluate to provide a positively charged eluate and bind portion of the phospholipids;

e. passing the positively charged eluate through a second crash membrane to remove a further portion of the phospholipids and interfering compounds to provide a second eluate;

f. introducing the second eluate to the second sorbent zone further bind phospholipids to provide a second sorbent zone eluate depleted in phospholipids; and g. passing the second sorbent zone eluate through the lower membrane zone to provide a third eluate being essentially free of phospholipids and interfering compounds; and, h. withdrawing the third eluate for further analysis of the metabolites of vitamin D or small molecules.

16. The process of claim 15, wherein the extraction reagent comprises a volume mix ratio of between 0.8 methanol:1.2 acetonitrile and 1.2 methanol:0.8 acetonitrile.

17. The process of claim 15, wherein the extraction reagent comprises a volume mix ratio of 1 methanol:1 acetonitrile.

18. The process of claim 15, wherein the dispensing of the serum or plasma sample to the introduction zone provides a volume E/S ratio of extraction reagent to said serum or plasma sample in the introduction zone ranging from about 6:1 to about 3:1.

19. The process of claim 18, wherein the volume E/S ratio of extraction reagent to said serum or plasma sample ranges from about 4.2:1 to about 3.8:1.

20. The process of claim 15, wherein the cation exchanged silica sorbent comprises a strong cation bonded to silica.

21. The process of claim 15, wherein at least 90 wt-% of the phospholipids are removed from the serum or plasma sample.

22. The process of claim 15, wherein the metabolites of vitamin D are selected from the group consisting of 1,25-dihydroxy vitamin D3, 25-hydroxy vitamin D2, 25-hydroxy vitamin D3, and mixtures thereof.

23. The process of claim 15, wherein the small molecules include caffeine, acetaminophen, hydrocortisone, and carbamazepine.

24. The process of claim 15, wherein the metabolites of vitamin D include of 1,25-dihydroxy vitamin D3 and recovery of 1,25-dihydroxy vitamin D3 is greater than 70 wt-percent.

25. The process of claim 15, wherein the concentration of the metabolites of vitamin D in the non-acidized serum or plasma sample ranges from about 10 to about 200 ng/mL.

26. The process of claim 15, wherein the concentration of 25-hydroxy vitamin D3 in the non-acidized serum or plasma sample ranges from about 5 to about 200 ng/mL.

27. The process of claim 15, wherein the concentration of 1,25-dihydroxy vitamin D3 in the non-acidized serum or plasma sample ranges from about 5 to about 200 ng/mL.

28. A kit for isolating metabolites of vitamin D or small molecules from a non-acidized serum or plasma sample comprising the apparatus of claim 1.

* * * * *